United States Patent [19]

Kawamura

[11] Patent Number: 5,228,457
[45] Date of Patent: Jul. 20, 1993

[54] PROTECTOR FOR HEARTBEAT-SYNCHRONOUS PULSE WAVE DETECTING PROBE

[75] Inventor: Norio Kawamura, Nagoya, Japan

[73] Assignee: Colin Electronics Co., Ltd., Aichi, Japan

[21] Appl. No.: 789,906

[22] Filed: Nov. 12, 1991

[30] Foreign Application Priority Data

Mar. 20, 1991 [JP] Japan .................................. 3-24863

[51] Int. Cl.⁵ .............................................. A61G 15/00
[52] U.S. Cl. .................................. 128/845; 128/846; 128/878; 5/607; 5/647
[58] Field of Search ............... 128/845, 846, 877, 878; 119/103; 5/607, 623, 624, 646, 647

[56] References Cited

U.S. PATENT DOCUMENTS

| | | | |
|---|---|---|---|
| 3,512,189 | 5/1970 | Swanson | 128/845 |
| 4,390,015 | 6/1983 | Clements | 5/650 |
| 4,766,892 | 8/1988 | Kreitman | 5/624 |

*Primary Examiner*—Randall L. Green
*Assistant Examiner*—Paul Prebilic
*Attorney, Agent, or Firm*—Oliff & Berridge

[57] ABSTRACT

A probe protector for protecting a heartbeat-synchronous pulse wave detecting probe set on a limb of a living subject, from contacting a medical staff attending to the subject on the side of the limb, the limb being supported on a support member having a side surface, the protector including (a) a flat portion adapted to be inserted between the support member, and a part of the limb on which part the detecting probe is set, the flat portion having a pair of opposite ends, (b) a protect portion extending from one of the opposite ends of the flat portion in a direction away from the flat portion, the protect portion protecting the detecting probe from contacting the medical staff, and (c) a stop portion extending from the one end of the flat portion in a direction opposite to the direction in which the protect portion extends, the stop portion being adapted to engage the side surface of the support member when the medical staff contacts the protect portion, so that the probe protector is prevented from being displaced more than a limited distance in the direction in which the medical staff moves.

4 Claims, 4 Drawing Sheets

PROTECTOR FOR HEARTBEAT-SYNCHRONOUS PULSE WAVE DETECTING PROBE

BACKGROUND OF THE INVENTION

1. Field of the Invention

The present invention relates to a protector for protecting a heartbeat-synchronous pulse wave detecting probe used on a limb of a living subject which limb is supported on a support member, from contacting a medical staff such as a doctor or nurse.

2. Related Art Statement

For monitoring blood pressure, or detecting arterial pulse wave, of a patient during, or after, a surgical operation, it is practiced to set a probe on a limb of the patient lying on an operating table and thereby detect pulse waves produced from the patient in synchronism with his or her heartbeat. Such heartbeat-synchronous pulse wave detecting probes include, for example, an inflatable cuff used for measuring blood pressure of a subject by detecting "oscillometric" pulse wave, or Korotkoff sound, produced from an upper arm or thigh when the air pressure in the cuff is changed, and a pulse wave sensor adapted to be set on a wrist of a subject for detecting pressure pulse wave produced from a radial artery in the wrist with the artery being partially flattened under the sensor.

When a doctor or nurse attends to the patient on the side of the limb on which the pulse wave detecting probe is set, during or after the surgical operation, the doctor or nurse may contact the probe, thereby displacing the probe or even causing noise to be mixed with the pulse wave from the probe. These problems lead to lowering the accuracy of detection of the pulse wave. However, if the medical staff perform his or her work by taking care not to contact the pulse wave probe for avoiding those problems, then the efficiency of performance of the work is lowered.

SUMMARY OF THE INVENTION

It is therefore an object of the present invention to provide a probe protector for protecting a heartbeat-synchronous pulse wave detecting probe worn on a limb of a subject which limb is supported on a support member, from contacting a medical staff attending to the subject on or from the side of the limb or the probe worn thereon.

The above object has been achieved by the present invention, which provides a probe protector for protecting a heartbeat-synchronous pulse wave detecting probe set on a limb of a living subject, from contacting a medical staff attending to the subject on the side of the limb, the limb being supported on a support member having a side surface, the protector comprising (a) means for providing a flat portion adapted to be inserted between the support member, and a part of the limb on which part the detecting probe is set, the flat portion having a pair of opposite ends, (b) means for providing a protect portion extending from one of the opposite ends of the flat portion in a direction away from the flat portion, the protect portion protecting the detecting probe from contacting the medical staff, and means for providing a stop portion extending from the one end of the flat portion in a direction opposite to the direction in which the protect portion extends, the stop portion being adapted to engage the side surface of the support member when the medical staff contacts the protect portion, so that the probe protector is prevented from being displaced more than a limited distance in the direction in which the medical staff moves.

The probe protector constructed as described above is used such that, with the protect portion being directed toward the medical staff, the flat portion is inserted between the support member, and the part of the limb on which the detecting probe is set, to the extent that the stop portion is brought into contact with the side surface of the support member. In this condition, the protect portion of the protector serves for protecting the detecting probe from contacting the medical staff, who attends to the subject on the side of the probe set on the limb of the subject supported on the support member. Thus, the present protector advantageously prevents the detecting probe from contacting the medical staff, thereby preventing the pulse wave detected by the probe from adversely being influenced by such contact.

In addition, since the stop portion engages the side surface of the support member when the medical staff contacts the protect portion, the protector is prevented from being displaced more than a limited distance in the direction in which the medical staff moves. Thus, the present protector assures that the detection of pulse wave by the probe is free from adverse influences from displacements of the probe.

Therefore, the medical staff can carry out his or her operation or treatment on the subject without having to take care not to contact the detecting probe or the protect portion of the protector. Thus, the medical staff can perform his or her work with higher efficiency than where no such protector is used and accordingly great care is needed not to contact the pulse wave detecting probe.

According to a preferred feature of the present invention, the means for providing the flat and protect portions comprise a first member having a generally J-shaped cross section, the flat portion corresponding to a straight portion of the J-shaped first member, the protect portion corresponding to a curved portion of the J-shaped first member. The first member may be formed of a resin.

According to another feature of the present invention, the means for providing the stop portion comprises a second member having a generally L-shaped cross section, the stop portion corresponding to a shorter straight portion of the L-shaped second member extending from a longer straight portion thereof, the second member being fixed to the first member such that the curved portion of the first member and the shorter straight portion of the second member extend in opposite directions, respectively. The second member may be formed of a metal.

According to yet another feature of the present invention, the protector further comprises first fastening means including a first fastener member fixed to on one of opposite surfaces of the protect portion which one surface is remoter than the other surface thereof from the flat portion, and second fastening means including an elongate, flexible second fastener member fixed at one of length-wise ends thereof to the flat portion such that the one end of the second fastener member is spaced apart from the stop portion, the second fastener member being engageable at the other length-wise end thereof with the first fastener member such that an intermediate portion of the second fastener member is wound around the support member and the stop portion which are in contact with each other.

According to a further feature of the present invention, the protector further comprises cushioning means provided on one of opposite surfaces of the flat portion which one surface is remoter than the other surface thereof from the second member, the one surface of the flat portion supporting, via the cushioning means, the limb of the subject on which the detecting probe is set.

BRIEF DESCRIPTION OF THE DRAWINGS

The above and optional objects, features and advantages of the present invention will be better understood by reading the following detailed description of the presently preferred embodiments of the invention when considered in conjunction with the accompanying drawings, in which.

DETAILED DESCRIPTION OF THE PREFERRED EMBODIMENTS

Figure 1:
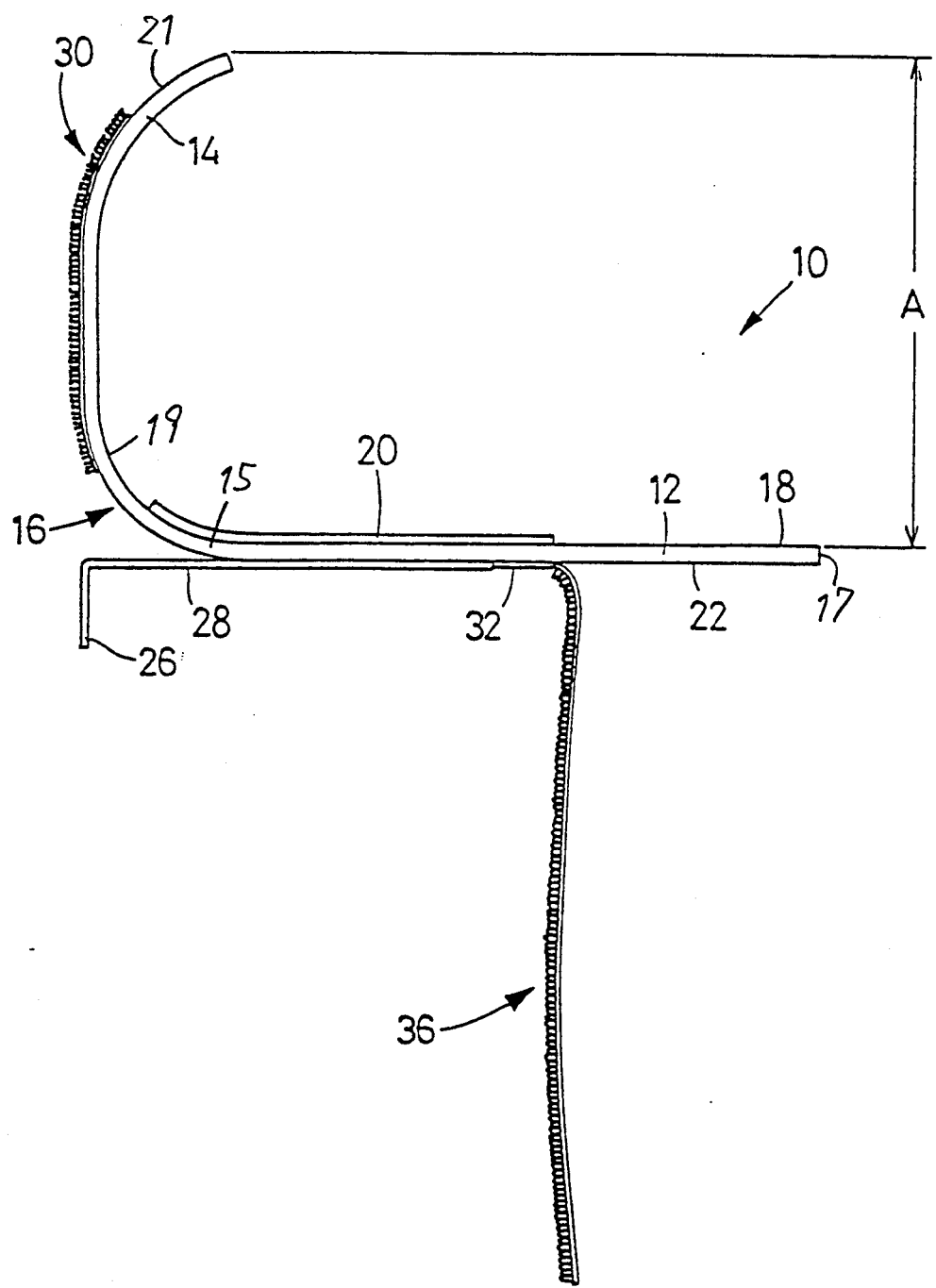
FIG. 1 is a front elevational view of a probe protector according to the present invention.
Figure 2:
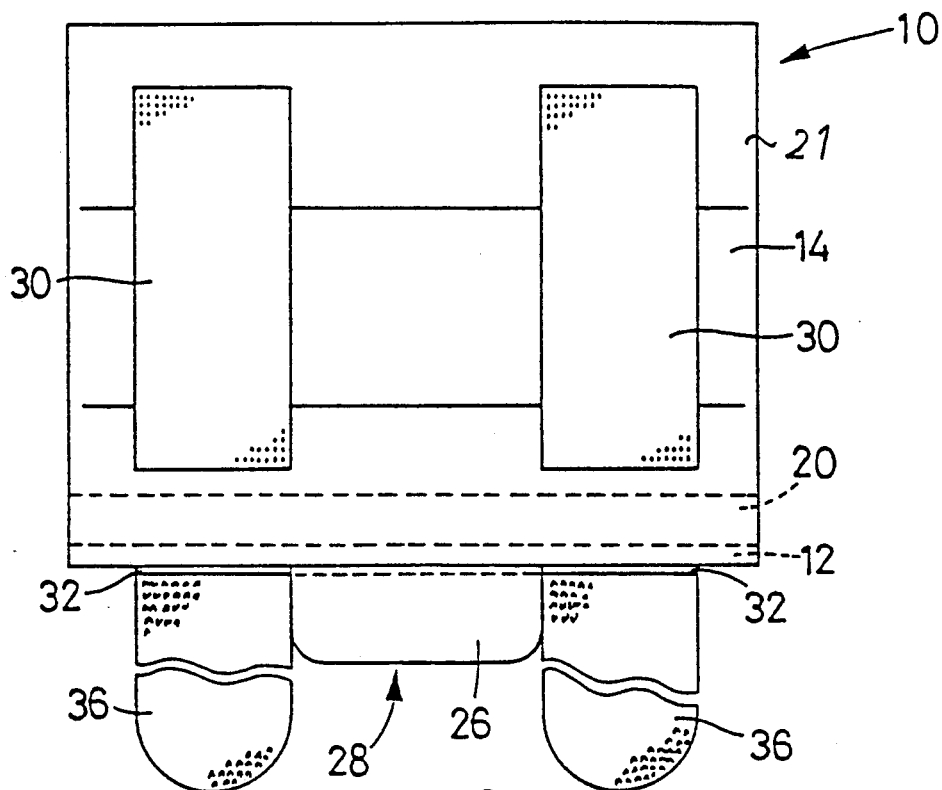
FIG. 2 is a side elevational view of the protector of FIG. 1, with a part thereof removed.
Figure 3:
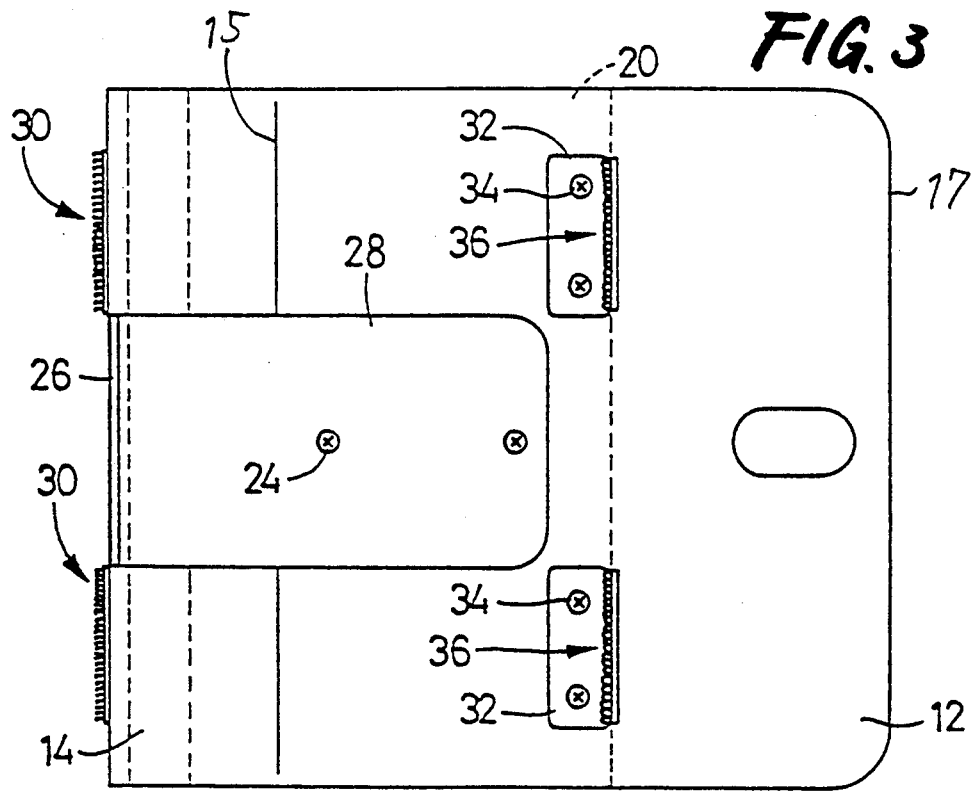
FIG. 3 is a bottom view of the protector of FIG. 1.

Referring first to FIGS. 1 through 3, there is shown a probe protector 10 embodying the present invention. The protector 10 includes a main body or first member 16 formed of, for example, transparent hard vinyl chloride resin, and a second member 28 formed of plate-like metal. The first member 16 includes a plate-like flat portion 12 having a generally rectangular shape, and a curved portion 14 extending from one of opposite ends 15, 17 of the flat portion 12 in a direction generally perpendicular to the plane of the flat portion 12. The thickness of the curved portion 14 is equal to that of the plate-like flat portion 12. The flat and curved portions 12, 14 are formed as the integral first member 16. Thus, the first member 16 has a J-shaped cross section. The second member 28 has a generally rectangular shape, and is secured with a pair of flat countersunk head screws 24, 24 to an intermediate portion of an outer surface (i.e., lower surface in FIG. 1) 22 of the flat portion 12 of the first member 16, as seen in a direction perpendicular to the direction in which the two ends 15, 17 of the flat portion 12 are opposite to each other (hereinafter, referred to as the "direction X"). The second member 28 includes a bent portion 26 at one of opposite ends thereof which one end corresponds to the one end 15 of the flat portion 12 from which the curved portion 14 extends. The bend portion 26 extends in a direction opposite to the direction in which the curved portion 14 extends. The protector 10 further includes a sponge member 20 fixed to a large portion of an inner surface 18 of the flat portion 12 which portion is located on the side of the curved portion 14, and a small portion of an inner surface 19 of the curved portion 14 which portion is continuous with the inner surface 18 of the flat portion 12. In addition, the protector 10 includes a pair of male fastener members 30, 30, and a pair of elongate flexible female fastener members 36, 36. The pair of male fastener members 30, 30 are fixed to an outer surface 21 of the curved portion 14, such that the male fasteners 30, 30 are spaced apart from each other in the direction X. Each female fastener member 36, 36 is fixed at one of lengthwise ends thereof to the outer surface 22 of the flat portion 12, with a pair of flat countersunk head screws 34, 34 via a clamp plate 32. The fixed ends of the female fasteners 36, 36 are positioned on both sides of, and adjacent to, the other end of the second member 28 than the one end thereof from which the bent portion 26 extends.

Figure 4:
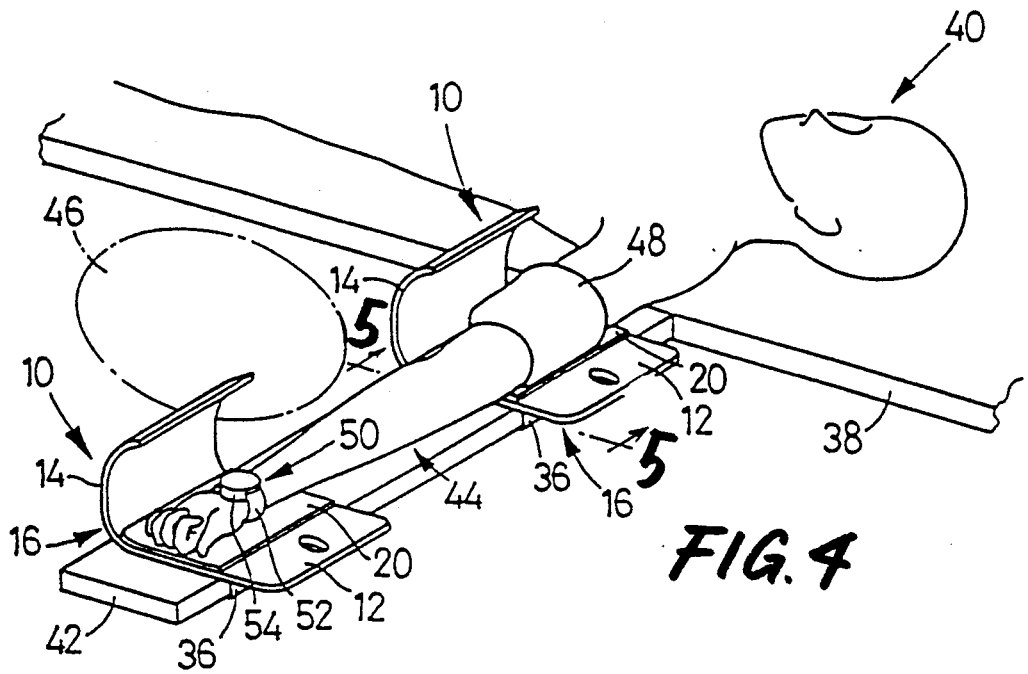
FIG. 4 is a view for illustrating the manner of use of the protector of FIG. 1.
Figure 5:
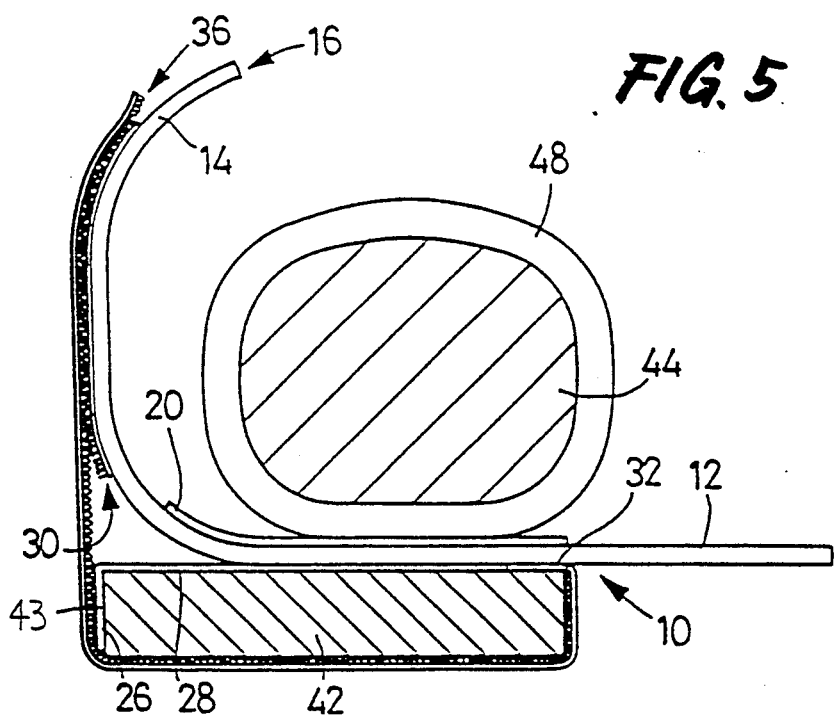
FIG. 5 is a cross sectional view taken along line 5—5 of FIG. 4.

Referring next to FIGS. 4 and 5, there will be described the use of the probe protector 10 constructed as described above.

FIG. 4 shows that a patient 40 is lying on his or her back on an operating table 38. An arm support 42 is secured to the side surface of the operating table 38 such that the upper surface of the arm support 42 is flush with the upper surface of the operating table 38. The arm support 42 has an elongate rectangular configuration. The arm support 42 supports a left arm 44 of the patient 40. A doctor 46 who is indicated by phantom line in FIG. 4 attends to the patient 40 on or from the side of the arm support 42. For example, the doctor 46 carries out a surgical operation with respect to the chest or abdomen of the patient 40. An inflatable cuff 48 used for measuring blood pressure is wound around an upper portion of the arm 44 of the patient 40, while a pulse wave sensor 50 is set on a wrist of the arm 44 with the help of a band 52. The upper arm of the patient 40 is pressed by the cuff 48 when the cuff 48 is supplied with pressurized fluid such as pressurized air from a pressure supply (not shown). When the fluid pressure in the cuff 48, that is, pressing force applied to the underlying, brachial artery in the upper arm of the patient 40 is changed, a systolic and a diastolic blood pressure of the patient 40 are measured based on pulse wave, or Korotkoff sound, produced from the brachial artery in synchronism with heartbeat of the patient 40. Meanwhile, the pulse wave sensor 50 includes a cylindrical housing 54 and a pressure transducer (not shown) accommodated in the housing 54. The housing 54 has a bottom wall and an opening, and the pressure transducer is advanceable from the opening of the housing 54. The pressure transducer is advanced from the housing 54 so as to be pressed against the radial artery via skin tissue. In this condition, the pressure transducer detects pressure pulse wave produced in the radial artery in synchronism with heartbeat of the patient 40. A pulse wave sensor disclosed in Japanese Patent Application laid open under Publication No. 3(1991)-7140 on Jan. 14, 1991, may be employed in the present embodiment. In the present embodiment, the patient 40 serves as a living subject, the left arm 44 of the patient 40 serves as a limb of the subject, and the doctor 46 serves as a medical staff attending to the subject. In addition, the arm support 42 serves as a support member for supporting the limb of the subject, and each of the cuff 48 and the pulse wave sensor 50 serves as a heartbeat-synchronous pulse wave detecting probe. Further description of the blood pressure measurement using the cuff 48 or the pressure pulse wave detection using the sensor 50 is omitted since it is well known in the art and is not so important for understanding the present invention.

As shown in FIGS. 4 and 5, two probe protectors 10, 10 are used on the arm support 42 for respectively preventing the two probes (cuff 48 and sensor 50) set on the arm 44, from contacting the doctor 46. More specifically described, first, the flat portion 12 of the first member 16 of each protector 10 is inserted between the upper portion or wrist of the arm 44 and the arm support 42, with the curved portion 14 being directed toward the doctor 46, to the extent that the bent portion 26 of the second member 28 is brought into contact with a side surface 43 of the arm support 42. Subsequently, the cuff 10 and the sensor 50 are set on the upper portion and wrist of the left arm 44, respectively, and then the cuff 10 and the band 52 are placed onto the sponge member 20 provided on the inner surface 18 of the flat portion 12. Further, the two female fastener members 36, 36 are wound around the arm support 42 and bent portion 26 held in contact with each other, so as to engage the corresponding male fastener members 30, 30 with a suitable tension force being produced in the flexible female fasteners 36, 36. In this situation, the probe protectors 10, 10 are surely prevented from being displaced in a direction from the one end 15 of the flat portion 12 toward the other end 17 thereof, even if the doctor 46 contacts the curved portion 14. In addition, the probe protectors 10, 10 are prevented from being displaced both in an opposite direction from the other end 17 of the flat portion 12 toward the one end 15 thereof and in a direction perpendicular to the opposite directions, that is, length-wise direction of the arm support 42. The height of the curved portion 14 as measured from the level of the inner surface 18 of the flat portion 12, indicated at A in FIG. 1, is selected at, for example, 160 to 170 mm, so that the curved portion 14 effectively protects the cuff 48 and sensor 50 set on the arm 44, from contacting the doctor 46. In the present embodiment, the flat portion 12 serves as means for providing a flat portion to be inserted between the support member and the limb of the subject, the curved portion serves as means for providing a protect portion for protecting the probe from contacting the medical staff, and the bent portion 26 serves as means for providing a stop portion adapted to engage the side surface of the support member.

As is apparent from the foregoing description, when the doctor 46 performs a surgical operation on the patient 40 on the side of the arm 44 (or arm support 42) while the cuff 48 and the pulse wave sensor 50 set on the left arm 44 are used for detecting the pulse wave or Korotkoff sound and detecting the pressure pulse wave, respectively, the curved portions 14 of the protectors 10 serve for protecting the cuff and sensor 50 from contacting the doctor 46 who is moving around the patient 40. Thus, the protectors 10 prevent the pulse wave or Korotkoff sound detected from the brachial artery, or blood pressure determined based thereon, and the pressure pulse wave detected from the radial artery, from adversely being influenced by contact between the doctor 46 and the cuff 48 or sensor 50 set on the arm 44 of the patient 40.

In the present embodiment, the protector 10 is secured to the arm support 42 by a sufficiently great fastening force produced by the engaged male and female fasteners 30, 36, with the bent portion 26 of the second member 28 being in contact with the side surface 43 of the arm support 42. Therefore, when the doctor 46 contacts the curved portion 14 of the first member 16 of the protector 10, the first member 16, fixed to the second member 28, is surely prevented from being displaced more than a limited distance in the direction in which the doctor 46 moves. In addition, the first member 16 is prevented from being displaced in the direction toward the doctor 46 and in the length-wise direction of the arm support 42. This arrangement contributes to preventing the blood pressure measurement or pressure pulse wave detection from adversely being influenced by displacement of the protector 10 or first member 16 thereof.

By using the protector or protectors 10, the doctor 46 can perform his or her operation without having to take care not to contact the cuff 48 or pulse wave sensor 50, so that the doctor 46 can concentrate on the operation. Thus, the protector 10 assures that the doctor 46 performs his or her operation with higher efficiency than where no such protector is used.

In the present embodiment the cuff 48 and band 52 (sensor 50) set on the arm 44 of the patient 40 are supported on the sponge member 20 provided on the upper surface 18 of the flat portion 12. The sponge member 20 absorbs vibration transmitted to the arm 44, thereby advantageously reducing motion of the arm 44.

The present embodiment provides another advantage that, since the protector 10 is secured to the arm support 42 by the male and female fasteners 30, 36 engaged with each other, the protector 10 is easily secured to the support 42 at appropriate positions along the elongate support 42 for individual patients having different arm lengths. In addition, regarding various arm supports having different cross sectional areas or different peripheral lengths, the protector 10 is easily secured thereto.

While in the present embodiment the curved portion 14 of the first member 16 serves as the protect portion of the protector 10, it is possible to use, in place of the curved portion 14, a second flat portion or member extending in a direction perpendicular, or with an acute angle, to the plane of the first flat portion 12.

Although in the present embodiment the flat and curved portions 12, 14 are formed of a resin into the integral first member 16, it is possible to form an integral first member 16 of a metal. Alternatively, it is possible to form, in place of the integral first member 16, a flat and a curved (or flat) member independent of each other, and fix the two members to each other to provide a first member 16.

While in the present embodiment the second member 28 fixed to the first member 16 serves as the stop portion of the protector 10, the stop portion may be formed integrally with a first member 16, by using a suitable material such as resin or metal.

In addition, in place of the male and female fasteners 30, 36 used for securing the protector 10 to the arm support 42, it is possible to use an extension extending from the free end of the bent portion 26 of the second member 28 in a direction toward one end of the second member 28 which is opposite to the other end thereof from which the bent portion 26 extends. In this case, the extension and a portion of the second member which portion is opposed to the extension cooperate with each other to hold or grasp the side portion of the arm support 42 therebetween. Alternatively, the bent portion 26 may be secured to the arm support 42 by using a screw or screws.

For protecting the peripheral edge lines of the curved portion 14 of the first member 16, a soft material such as soft vinyl may be used to cover the edge lines.

In the present embodiment, the sponge member 20 is provided on the flat portion 12 of the first member 16. However, the sponge member 20 may be omitted. Alternatively, it is possible to use a soft rubber plate in place of the sponge 20.

In the present embodiment, two protectors 10 are used for protecting the cuff 48 and the pulse wave sensor 50 each as the heartbeat-synchronous pulse wave detecting probe. However, it is possible that a single protector 10 be used for the cuff 48 or the sensor 50. Otherwise, a protector 10 may be used for protecting an oximeter probe which optically detects a heartbeat-synchronous pulse wave for monitoring blood oxygen saturation of a subject. The oximeter probe may be used in addition to the cuff 48 and sensor 50, or in place of the cuff 48 and sensor 50 or one of the two probes 48, 50, and be set on a finger of the patient 40. In the case where the oximeter probe is used together with the pulse wave sensor 50, a common single protector 10 may be used for protecting both of the two probes.

Figure 6:
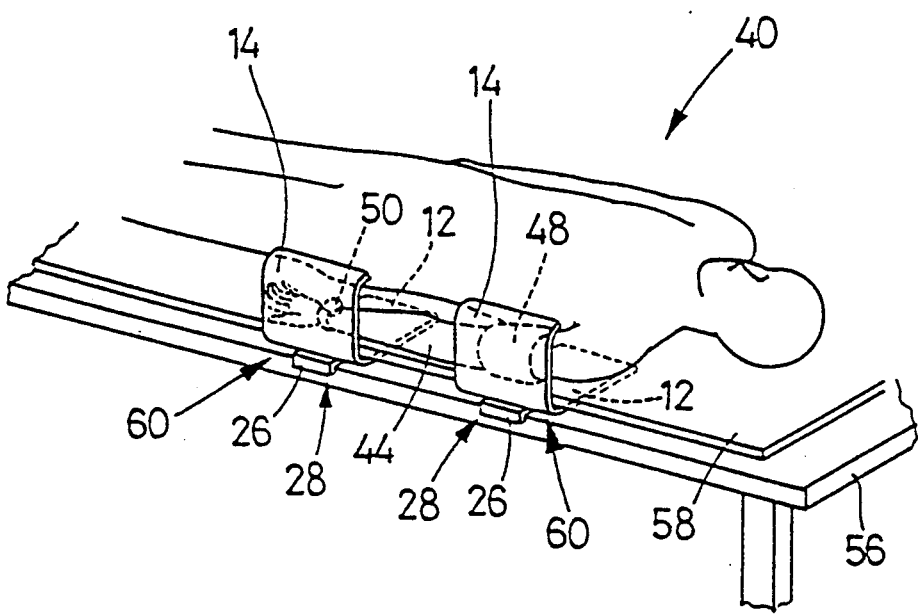
FIG. 6 is a view of a probe protector as another embodiment of the present invention, illustrating the manner of use of the protector.

Referring next to FIG. 6, there is shown another embodiment of the present invention. While the preceding or first embodiment relates to the case where the arm 44 of the patient 40 is supported on the arm support 42 extending in a direction perpendicular to the operating table 38, the instant or second embodiment relates to the case where a left arm 44 of a patient 40 is supported on a mat 58 on which the patient 40 lies on his or her back. A cuff 48 and a pulse wave sensor 50 are set on the arm 44, and a doctor 46 performs a surgical operation on the side of the arm 44 of the subject 40. In this case, two protectors 60 are used for protecting the cuff 48 and the sensor 50, respectively. The protectors 60 have the same construction as that of the protectors 10 of the first embodiment, except that the protectors 60 do not have the male and female fastener members 30, 36. Flat portions 12 of the two protectors 60 are inserted between the mat 58 and an operating table 56 on which the mat 58 is extended, to the extent that bent portions 26 of the protectors 60 are brought into contact with a side surface 57 of the operating table 56. Thus, the curved portions 14 of the two protectors 60 are aligned with the cuff 48 and the sensor 50, respectively. In the instant embodiment, the operating table 56 serves as the support member for supporting a limb of a subject. In the present case, the protectors 10 of the first embodiment may be used in place of the protectors 60.

Furthermore, a probe protector according to the present invention is useful for protecting a heartbeat-synchronous pulse wave detecting probe set on an arm of a patient lying on his or her face, or a leg of a patient lying on the back or face, from contacting a doctor attending to the patient on the side of the detecting probe.

In addition, the probe protector of the present invention is applicable to cases where doctors or nurses carry out various kinds of medical operations or treatments other than surgical operations.

While the present invention has been described in its presently preferred embodiments with particular details, it is to be understood that the present invention may be embodied with various changes, improvements and modifications that may occur to those skilled in the art without departing from the scope and spirit of the invention defined in the appended claims.

What is claimed is:

1. A probe protector for protecting a heartbeat-synchronous pulse wave detecting probe set on a limb of a living subject, from contacting a medical staff attending to the subject on the side of the limb, the limb being supported on a support member having a side surface, the probe protector comprising:

means for providing a flat portion adapted to be inserted between said support member and a part of said limb on which part said detecting probe is set, said flat portion having a pair of opposite ends;

means for providing a protect portion extending from one of said opposite ends of said flat portion in a direction away from said flat portion, said protect portion protecting said detecting probe from contacting said medical staff;

said means for providing said flat and protect portions comprising a first member having a generally J-shaped cross section, said flat portion corresponding to a straight portion of the J-shaped first member, said protect portion corresponding to a curved portion of the J-shaped first member;

means for providing a stop portion extending from said one end of said flat portion in a direction opposite to the direction in which said protect portion extends, said stop portion being adapted to engage the side surface of said support member when said medical staff contacts said protect portion, so that the probe protector is prevent from being displaced more than a limited distance in the direction in which said medical staff moves;

said means for providing said stop portion comprising a second member having a generally L-shaped cross section, said stop portion corresponding to a shorter straight portion of the L-shaped second member extending from a longer straight portion thereof, said second member being fixed to said member such that said curved portion of said first member and said shorter straight portion of said second member extend in opposite directions, respectively;

first fastening means including a first fastener member fixed to one of opposite surfaces of said protect portion which one surface is more remote than the other surface thereof from said flat portion; and second fastening means including an elongate, flexible second fastener member fixed at one of lengthwise ends thereof to said flat portion such that said one end of said second fastener member is spaced apart from said stop portion, said second fastener member being engageable at the other length-wise end thereof with said first fastener member such that an intermediate portion of said second fastener member is held in contact with said support member and said stop portion, so that said first and second fastener members cooperate with each other to fasten the probe protector on said support member.

2. A probe protector according to claim 1, wherein said first member is formed of a resin.

3. A probe protector according to claim 1, wherein said second member is formed of a metal.

4. A probe protector according to claim 1, further comprising cushioning means provided on one of opposite surfaces of said flat portion which one surface is remoter than the other surface thereof from said second member, said one surface of said flat portion supporting, via said cushioning means, said limb of said subject on which the detecting probe is set.

* * * * *